US007715571B2

(12) United States Patent
Boretzki et al.

(10) Patent No.: US 7,715,571 B2
(45) Date of Patent: May 11, 2010

(54) METHOD FOR INDIVIDUALLY FITTING A HEARING INSTRUMENT

(75) Inventors: Michael Boretzki, Rueti (CH); Volker Kuehnel, Maennedorf (CH); Andreas Von Buol, Zurich (CH); Paul Zbinden, Hombrechitkon (CH)

(73) Assignee: Phonak AG, Staefa (CH)

( * ) Notice: Subject to any disclaimer, the term of this patent is extended or adjusted under 35 U.S.C. 154(b) by 1082 days.

(21) Appl. No.: 11/277,237

(22) Filed: Mar. 23, 2006

(65) Prior Publication Data

US 2007/0223752 A1 Sep. 27, 2007

(51) Int. Cl.
*H04R 29/00* (2006.01)
*H04R 25/00* (2006.01)
*A61B 5/00* (2006.01)

(52) U.S. Cl. ......................... 381/60; 381/312; 381/320; 600/559

(58) Field of Classification Search ................... 381/60, 381/312, 320
See application file for complete search history.

(56) References Cited

U.S. PATENT DOCUMENTS 4,099,035 A 7/1978 Yanick
4,471,171 A 9/1984 Köpke et al.
4,548,082 A * 10/1985 Engebretson et al. ......... 73/585
4,577,641 A * 3/1986 Hochmair et al. ........... 600/559
6,201,875 B1 * 3/2001 Davis et al. ................. 381/314
6,315,710 B1 11/2001 Bushek et al.
6,554,762 B2 4/2003 Leysieffer
6,574,342 B1 6/2003 Davis et al.
6,788,790 B1 9/2004 Leysieffer
2002/0026091 A1 * 2/2002 Leysieffer .................... 600/25

FOREIGN PATENT DOCUMENTS

EP 0 535 425 B1 4/1993
EP 0 661 905 B1 7/1995
WO 00 65872 A1 11/2000
WO 2004 054318 A1 6/2004

* cited by examiner

*Primary Examiner*—Brian Ensey
*Assistant Examiner*—Sunita Joshi
(74) *Attorney, Agent, or Firm*—David S. Safran; Roberts Mlotkowski Safran & Cole, P.C.

(57) ABSTRACT

A method for individually fitting a hearing instrument to a user, by: starting operation of the hearing instrument; pre-defining a desired target loudness function perceived by the user defined as function of frequency and input sound pressure level at the microphone; measuring for a given measurement parameter set of perceived loudness levels and frequencies or frequency bands the respective transducer input audio signal level to be applied to the transducer input to achieve the respective perceived loudness level at the respective frequency or frequency band, said measurement parameter set having at least a low, intermediate and high loudness levels, and said intermediate loudness level being measured for a larger number of frequencies or frequency bands and with a finer frequency resolution than said low and high loudness levels; calculating an individual gain function to be implemented in the audio signal processing unit to achieve the pre-defined target loudness function by taking into account the measured transducer input audio signal levels; and operating the hearing instrument with the individual gain function.

40 Claims, 10 Drawing Sheets

METHOD FOR INDIVIDUALLY FITTING A HEARING INSTRUMENT

BACKGROUND OF THE INVENTION

1. Field of the Invention

The present invention relates to a method for individually fitting a hearing instrument.

2. Description of Related Art

A hearing instrument usually comprises a microphone for generating an input audio signal from ambient sound, an audio signal processing unit (which nowadays often is digital) for processing the input audio signal into a processed output audio signal and an output transducer for stimulation of the user's hearing according to the processed output audio signals. Audio signal processing in the audio signal processing unit involves applying a gain function to the input audio signal, which depends on level and frequency of the input audio signal. Hearing instruments usually are used by persons suffering from a hearing loss compared to normal-hearing persons, which depends on level and frequency of the ambient sound. Usually the hearing instrument undergoes a fitting procedure in order to individually set the gain provided by the hearing instrument such that the hearing loss of the user is compensated as far as possible.

In the prior art various attempts have been made for the fitting of hearing aids to the needs of an individual patient.

U.S. Pat. No. 4,577,641 relates to a fitting process for a cochlear implant wherein equal loudness contour (ELC) measurements are conducted after the device has been implanted in order to determine the individual optimized gain function of the hearing instrument. The ELC measurements are carried out at the most comfortable loudness level.

U.S. Pat. No. 4,471,171 relates to a hearing instrument with an electroacoustic output transducer, wherein a sound generator is integrated within the hearing instrument for performing hearing threshold measurements as a function of frequency.

U.S. Pat. No. 6,788,790 relates to the integration of a sound generator for audiometric measurement within a partially or fully implantable hearing instrument for e.g. direct mechanical stimulation of the inner ear.

According to EP 0 535 425 B1 loudness curves as a function of the sound input level are measured for various frequencies. From these loudness curves contours of equal loudness as a function of frequency are plotted for various loudness values. However, the loudness curves are obtained without the hearing aid being used.

US 2002/026091 A1 relates to an implanted hearing instrument with an electromechanical transducer, wherein the quality of the coupling between the transducer and the user's ear is evaluated by measuring the mechanical impedance after implantation of the transducer.

EP 0 661 905 B1 relates to a fitting model for hearing aids in order to take into account various psycho-acoustic effects, i.e. in order to take into account the fact that loudness curves are measured with sinus tones or low-band noise while practical ambient sound, in particular speech, is perceived by the user in a much more complex manner than sinus tones or narrow-band noise.

Fitting procedures for hearing instruments with electroacoustic output transducers are suggested in U.S. Pat. No. 6,574,342 B1 and U.S. Pat. No. 6,201,875 B1 which propose to perform measurements of the contours of equal loudness with the hearing instrument worn by the user and with the stimuli created by the hearing instrument itself. In these measurements, for a plurality of frequencies f or frequency bands, the input level of the hearing instrument is varied such that the loudness perceived by the user is kept constant. This procedure is repeated for different values/categories of loudness ranging from very soft to extremely loud. The thus measured contours of equal loudness are used to determine the individual gain function which is finally implemented in the hearing instrument to compensate for the user's individual hearing loss.

While using the fitting procedures suggested in U.S. Pat. No. 6,574,342 B1 and U.S. Pat. No. 6,201,875 B1 the hearing device can be well fitted to the individual hearing loss experienced by the patient, these procedures are disadvantageous in that a large number of measurements has to be taken. In particular, in the fitting procedures described in U.S. Pat. No. 6,574,342 B1 and U.S. Pat. No. 6,201,875 B1 measurements are taken at 12 different frequencies for 7 different loudness levels. That means that 84 individual reading points are investigated, which necessitates a lengthy and troublesome procedure both for the patient and the physician or audiologist.

It is an object of the invention to provide for a simple and nevertheless accurate method for individually fitting a hearing instrument comprising an output transducer for stimulation of the human auditory system.

These and further objects, features and advantages of the present invention will become apparent from the following description when taken in connection with the accompanying drawings which, for purposes of illustration only, show several embodiments in accordance with the present invention.

SUMMARY OF THE INVENTION

According to the invention this object is achieved by a method as described below.

The solution according to a first aspect of the invention is beneficial in that, by measuring the perceived loudness at the intermediate loudness level for a larger number of frequencies or frequency bands and with a finer frequency resolution than at said low and high loudness levels and calculating the individual gain function to be implemented in the audio signal processing unit in order to achieve the pre-defined target loudness function using the transducer input audio signal levels taken during such measurements, the number of measurement points to be investigated can be substantially reduced.

The present invention takes advantage of the finding that the fine frequency dependency of the overall transfer function, i.e. that part of the frequency dependency which varies strongly/steeply within short frequency intervals (in other words, the short scale variations), is relatively similar for even significantly different perceived loudness levels of the signal. It has been found that thus, instead of individually determining the transfer functions for every single loudness category by taking measurements at a high frequency resolution for each loudness category of interest, it is usually sufficient to determine the transfer function only for a single intermediate loudness level at a higher frequency resolution, whereas for the low and high loudness levels measurement with low frequency resolution at only a few frequencies/frequency bands, i.e. at only a few measurement points is sufficient, since the actual short scale variations with frequency for those low and high loudness levels usually will be similar to that having been measured for the intermediate loudness level, which thus can be estimated by transferring that having been measured for the intermediate loudness level to the low and high loudness levels. Thus, having determined the frequency dependency of the overall transfer function by conducting measurements with a high frequency resolution at one loudness level, such as the most comfortable level (MCL), it is thus possible to quite precisely interpolate, preferably by linear interpolation, the frequency dependency also for loudness levels in which measurements were taken only for a few frequencies.

It is noted that the finding that the coupling transfer function from the output transducer to the user's hearing usually depends strongly on frequency but less on loudness level, while the hearing loss of the patient usually depends strongly on loudness level but less on frequency, enables separation of these two components by calculations so that common fitting software tools, which usually need these two components as separate input, can be used.

Preferably, in such measurements the intermediate loudness level is the most comfortable level, which may be from 60 to 70 phon and which is the input sound pressure level at which intelligibility of the stimulus by the user is best and to which the user could comfortably listen over an extended period of time. The low loudness level preferably is the hearing threshold, which is the input sound pressure level at which the stimulus becomes detectable by the user, and the high loudness level preferably is the uncomfortable level (UCL), which is the input sound pressure level at which loudness becomes uncomfortable to the user and the sensation could not be tolerated for an extended period of time.

Whereas for the intermediate loudness level the transducer input audio signal level should preferably be measured at at least 5 different frequencies or frequency bands, respectively, for at least one of the low loudness level and the high loudness level measurements at 3 to 5 frequencies or frequency bands can be sufficient in the practice of the invention. In the range of 0.75 to 3 kHz which is the range into which usually the resonance of an electromechanical output transducer falls so that the variation of the overall transfer function due to individual spread of the output transducer resonance can be eliminated, each contour of equal loudness preferably is measured at at least 5 different frequencies or frequency bands, respectively.

Preferably, in order to obtain a good frequency resolution, the transducer input audio signal level for the intermediate loudness level is measured for at least 8 frequencies or frequency bands. An even finer frequency resolution can be obtained by increasing the number of frequencies at which the loudness perception is measured, such as by measuring the transducer input audio signal level for the intermediate loudness level for at least 15 frequencies or frequency bands.

In a preferred embodiment of the invention the transducer input audio signal level is measured for each loudness level for frequencies or frequency bands in a range of from 100 to 10,000 Hz. Preferably, the frequencies or frequency bands are spaced in equal distances in the range of from 100 to 10,000 Hz.

In a particularly preferred embodiment of the invention the frequency dependence of the values of the transducer input audio signal level as measured for the intermediate loudness level is used to interpolate between the values of the transducer input audio signal level to be applied to the transducer input as measured for the low and the high loudness level. In this manner the present method enables to obtain functions representing the frequency dependency of the loudness perception at a high frequency resolution also for loudness categories in which readings are taken at a substantially lower frequency resolution, i.e. by taking measurements only for a few frequencies.

Preferably, the measurements for the intermediate loudness level are conducted as an equal loudness contour measurement, that is as a measurement wherein subsequently for each frequency or frequency band a transducer input audio signal level is selected which causes a constant level of loudness perception for the user.

Whereas for taking the measurements for the intermediate loudness level preferably narrow band noise is used, the measurements for the low and high loudness levels preferably are conducted with pure sinus tones. Instead of measuring—according to the first aspect of the invention—the transducer input audio signal level which has to be applied to the transducer input in order to achieve a certain intermediate perceived loudness level, according to a second aspect of the invention, a predetermined level of the processed output audio signal at a number of frequencies or frequency bands is present to the user and then the loudness level perceived by the user at the respective frequency or frequency band is measured. Using the thus obtained relationship between the level of the processed output audio signal, which is used as input signal for the transducer, and the perceived loudness level the overall transfer function can be determined.

In a preferred embodiment of the present invention transducer input audio signal levels are measured for the low and high loudness levels as an equal loudness contour measurement, wherein subsequently for each frequency or frequency band the transducer input audio signal level is selected such that the same loudness level is perceived by the user. Then a preliminary individual gain function is calculated by taking into account the measured transducer input audio signal levels for the low and high loudness levels, so as to achieve a pre-defined target loudness function which at least in a range of medium input sound pressure levels corresponds to the standard loudness function of a normal hearing person. In a further step, the contour of equal loudness is estimated for the intermediate loudness level from the preliminary individual gain function, and the individual gain function is calculated by correcting the preliminary individual gain function by taking into account the difference between the contour of equal loudness measured for the intermediate loudness and the estimated contour of equal loudness.

In this embodiment of the invention thus a two-stage fitting procedure is employed, wherein in-situ ELC measurements are made in the second stage, whereby a particularly simple but nevertheless accurate fitting procedure is provided which does not require knowledge of the transfer function of the components of the hearing instrument; in particular, it does not require knowledge the transfer function of the electromechanical or electroacoustical output transducer and the coupling to the user's anatomy. In particular, with the help of the ELC measurements in the second stage of the fitting procedure the hearing instrument can be compensated for the usually unknown and significantly spreading resonance of the electromechanical output transducer in the range of 0.75 to 3 kHz.

The reason for performing in this embodiment initial coarse audiogram measurements is to determine preliminary fitting parameters in order to enable accurate measurements of the contour of equal loudness in the second step, with the hearing instrument already being operated in a manner taking into account those preliminary fitting parameters (e.g. hearing threshold, MCL, UCL). Thereby it becomes possible to perform the contour of equal loudness measurements with the hearing instrument already being operated in a manner more or less close to the finally fitted hearing instrument.

Generally, the measurement of the contour of equal loudness should have a finer frequency resolution than the initial audiogram measurements, thereby serving as a correction of the initial, relatively coarse audiogram measurement. To this end, the number of frequencies or frequency bands at which the contour of equal loudness is measured preferably is larger than the number of frequencies or frequency bands at which the initial audiogram measurement is performed.

When estimating the contour of equal loudness from the initial loudness measurements, this can be done by linear interpolation between the measured frequencies or frequency bands, respectively.

Preferably, the initial audiogram measurements are performed with pure sinus tones, while the measurement of the contour of equal loudness is performed with narrow-band noise.

The target loudness function at least in the range of medium input sound pressure levels preferably corresponds to the standard loudness function of a normal hearing person. For medium input sound pressure levels an individual gain function thus can be determined by adding the difference between the standard loudness function of a normal hearing person and the initially determined individual loudness function being derived from the audiogram data to the preset standard gain function.

For low and high input sound pressure levels the gain in the target loudness function may be progressively reduced compared to the gain for medium input sound pressure levels, i.e. for low and high sound input pressure levels the gain may be smaller than the sum of the difference between the standard loudness function of a normal hearing person and the determined individual loudness function and the preset standard gain function. For low input sound pressure levels, the gain in the target loudness function may be progressively reduced towards low input sound pressure levels, while for high input sound pressure levels the gain in the target loudness function may be progressively reduced towards high input sound pressure levels. Above a given high input sound pressure level the gain may be reduced below zero in order to provide for a maximum power output limitation, so that the hearing instrument saturates at very high input sound pressure levels.

While the transducer input audio signal used in the measurements can be generated by providing corresponding sound to the microphone, preferably the stimulus is generated by the audio signal processing unit itself. To this end, the audio signal processing unit can be provided with a sound generator. Such measurements, which are more accurate and reproducible than earphone measurements, are made possible by the fact that usually the transfer function of ambient sound to the audio signal processing unit via the microphone is known.

According to a preferred embodiment, an electromechanical output transducer is used which is directly connected, via an artificial incus, with the stapes or the footplate of the stapes or with the round window or an artificial window of the cochlear wall. Such hearing instruments also are known as DACS (Direct Acoustic Cochlear Stimulator).

However, the fitting method according to the invention also can be used for hearing instruments with electroacoustic output transducer or for cochlea implants.

In the following, examples of the invention will be described in more detail by reference to the attached drawings.

BRIEF DESCRIPTION OF THE DRAWINGS

FIG. 11B shows the results obtained by the measurements taken at the hearing threshold (THR), wherein the data curve is obtained by interpolation between the measuring data using the curve shown in FIG. 11A.

DETAILED DESCRIPTION OF THE INVENTION

Figure 9:
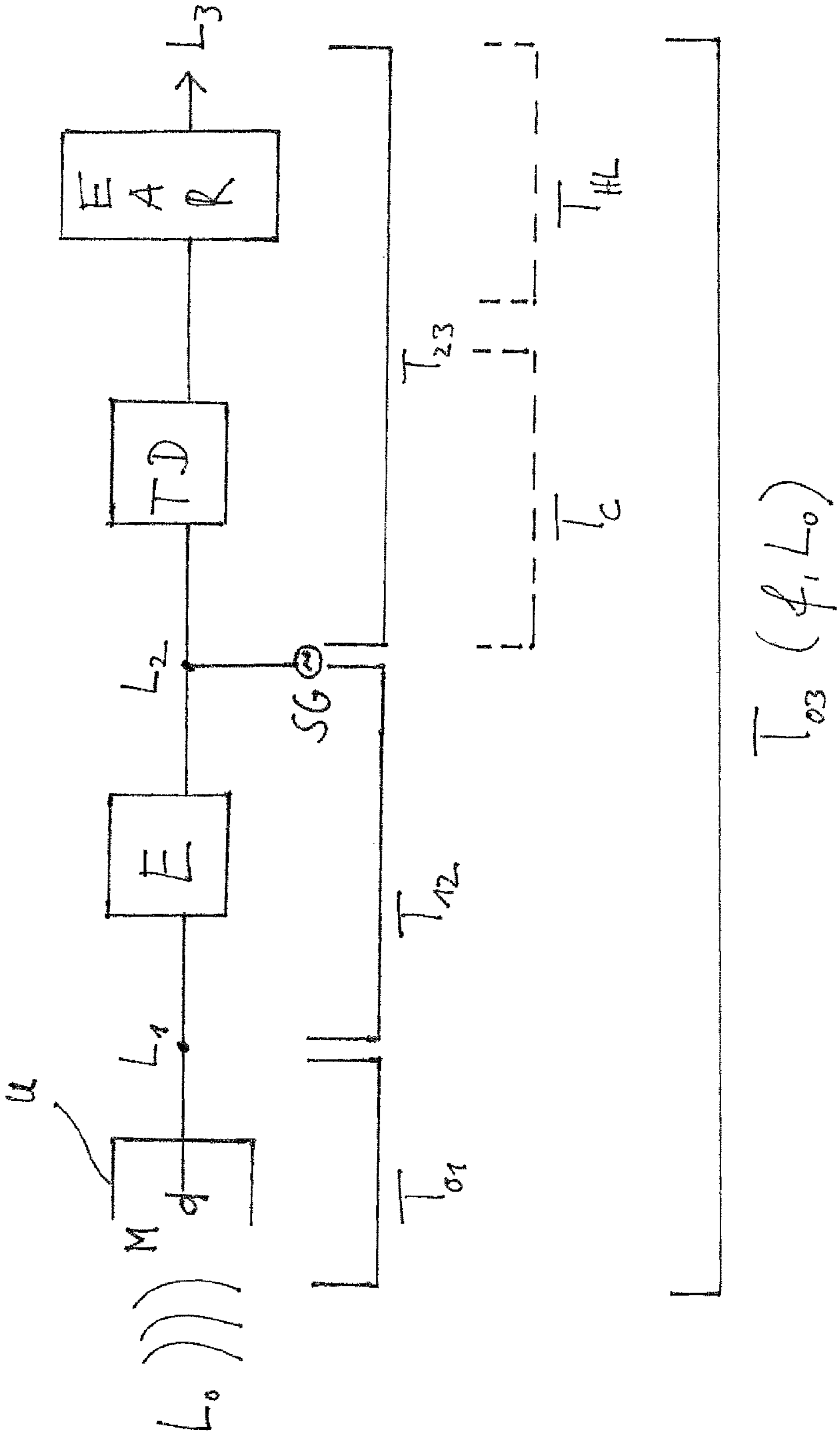
FIG. 9 is a diagram illustrating a signal conversion as performed in a hearing instrument.

To facilitate understanding of the fitting procedure, signal conversion as performed in a hearing instrument will be explained below by reference to FIG. 9. As it is schematically shown in FIG. 9 a sound level $L_0$ is applied to a microphone M which is arranged in an environment U. Microphone M converts the sound signal into an electric signal level $L_1$, which by means of an audio signal processing unit E is converted into an electric signal level $L_2$ to be applied as input signal to an output transducer TD. Output transducer TD, which can be an electroacoustic transducer (i.e. a speaker/receiver), an electrode for direct electric stimulation of the cochlea or an electromechanical output transducer for direct mechanical stimulation of the middle ear or the inner ear, and which in case that the output transducer TD is an electrode or an electromechanical output transducer has to be implanted, is coupled to the hearing apparatus EAR of the patient. In dependency of the type of output transducer used, the coupling, for example, may be acoustically via the tympanic membrane, or mechanically via the stapes or the oval window, so as to generate within the hearing apparatus EAR a stimulus which is perceived by the patient as loudness sensation $L_3$.

Conversion of the original sound level $L_0$ into the loudness sensation $L_3$ perceived by the patient involves a number of transfer functions which also are indicated in FIG. 9. In particular, conversion of the original sound level $L_0$ into the electric signal level $L_1$ is governed by a transfer function $T_{01}$ which basically is dependent on the frequency of the signal presented to the microphone and thus can be assumed to be known. The transfer function $T_{12}$ which describes conversion of electric signal level $L_1$ to processed electric signal level $L_2$ to be applied as input signal to output transducer TD can be adjusted by means of audio signal processing unit E. For audio signal measurements, instead of using an airborne sound signal to be picked up by microphone M, there can be provided a signal processor SG which feeds a known sound level $L_2$ to output transducer TD. The transfer function $T_{23}$ which associates a certain loudness perception to a certain input signal level $L_2$ of the transducer TD generally is not known and depends on the individual circumstances of the patient. In particular, transfer function $T_{23}$ combines a coupling portion $T_C$ which accounts for the transducer resonance and the coupling of the transducer to the anatomic structures of the patient as well as a hearing loss portion $T_{HL}$ which represents the individual hearing loss experienced by the patient. In order to be able to determine the overall transfer function $T_{03}$ by which conversion of a sound event into a hearing impression can be described and which is composed of the above partial transfer function $T_{01}$, $T_{12}$ and $T_{23}$, transfer function $T_{23}$ has to be determined in the course of the fitting procedure.

In view of the above the fitting procedure aims at adjusting the audio signal processing unit E (and hence transfer function $T_{12}$) such that the overall transfer function $T_{03}$ (and hence association of a certain loudness perception $L_3$ to a certain input signal level $L_2$) assumes a certain shape, which often, at least for intermediate loudness levels, approximates the overall transfer function $T_{03}$ that is realized in normal healthy hearing. For low and high loudness levels often an overall transfer function $T_{03}$ is preferred which differs from that achieved in normal hearing. Thus, whereas for low loudness levels often a so-called "Soft Squelch" function is implemented by which the gain function is progressively reduced towards low input sound levels, for high loudness levels many patients prefer a limitation of the loudness level, i.e. a compression of the gain function.

In the course of the fitting procedure first the initially unknown transfer function $T_{23}$ is determined with the aid of audiologic measurements. In a second step, using the known microphone transfer function $T_{01}$ and the required transfer function $T_{12}$ of the audio signal processing unit E as a function of loudness level and frequency, a desired overall transfer function $T_{03}$ can be calculated and implemented in the audio signal processing unit E.

Figure 1:
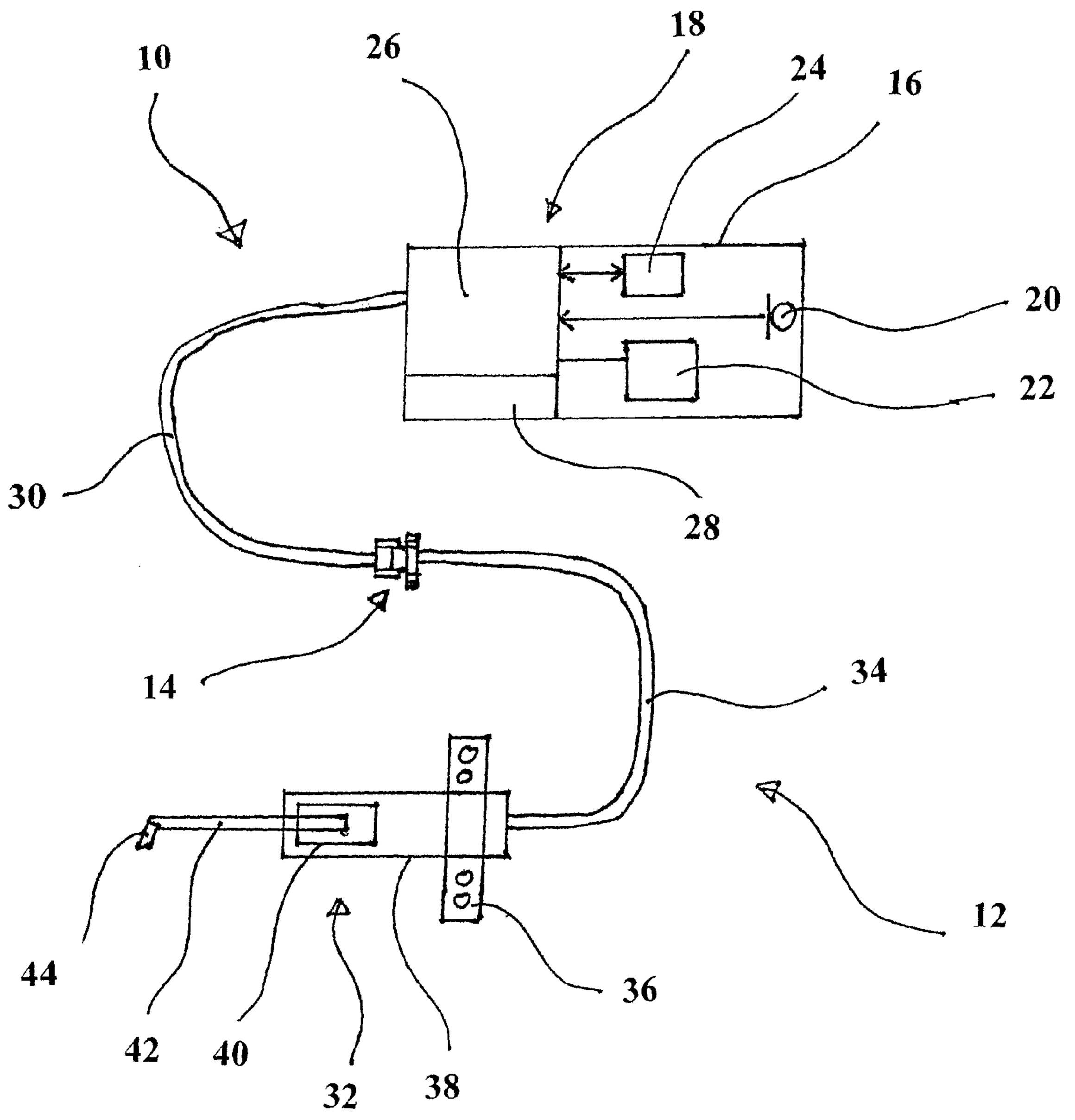
FIG. 1 is a schematic view of a hearing instrument according to the invention.

FIG. 1 is a schematic view of an example of a hearing instrument according to the invention comprising an external part 10 and an implantable part 12 which are connected via a percutaneous plug 14. The external part 10 comprises a housing 16 to be worn somewhere at the user's body, for example, behind the ear. The housing 16 forms a control unit 18 which comprises at least one microphone 20 for converting ambient sound into an input audio signal, a battery 22, a data memory 24 and a digital audio signal processing unit 26. The digital audio signal processing unit 26 is for processing the audio input signal provided by the microphone 20 into a processed output audio signal by applying a gain function, which depends on frequency and audio signal input level, to the input audio signal provided by the microphone 20. The gain function, together with other operating parameters and the operating program for the digital audio signal processing unit 26, may be stored in the memory 24. The digital audio signal processing unit also may comprise a sound generator 28. In an alternative embodiment the sound generator 28 may be provided separate from the digital audio signal processing unit 26.

The control unit 18 is connected to the percutaneous plug 14 via a tube 30 which houses wires for providing the output audio signal from the digital audio signal processing unit 26 to an electromechanical output transducer 32 and for supplying the electromechanical output transducer 32 with power from the battery 22. To this end, the output transducer 32 is electrically connected to the percutaneous plug 14 via a tube 34. The implantable part 12 consists of the output transducer 32, the tube 34 and the implantable part of the plug 14. The implantable part 12 is implanted into the skull of the user, with the output transducer 32 comprising a bone plate 36 which is fixed at the user's skull.

The output transducer comprises a housing 38 comprising a drive 40 for driving a rod 42 for reciprocating movement. The free end of the rod 42 is provided with an artificial incus 44 which is to be mechanically connected to the cochlea of the user. The fixation of the artificial incus 44 at the user's cochlea can be achieved by surgical techniques which are known as stapedotomy or stapedectomy. Conventionally, these techniques are used for connecting the artificial incus of a middle ear prosthesis to the patient's stapes (stapedotomy) or footplate of the stapes (stapedectomy) when treating otosclerosis.

The drive 40 may be an electromagnetic drive (an example of which is described in U.S. Pat. No. 6,315,710 B1) or a piezoelectric drive (an example of which is described in U.S. Pat. No. 6,554,762 B2).

The hearing instrument of FIG. 1 is particularly suited for patients who cannot be effectively treated with electroacoustic hearing aids alone and therefore would require surgery anyhow. The hearing instrument used in the present invention completely bypasses the middle ear and thus does not require a functional middle ear.

Figure 2:
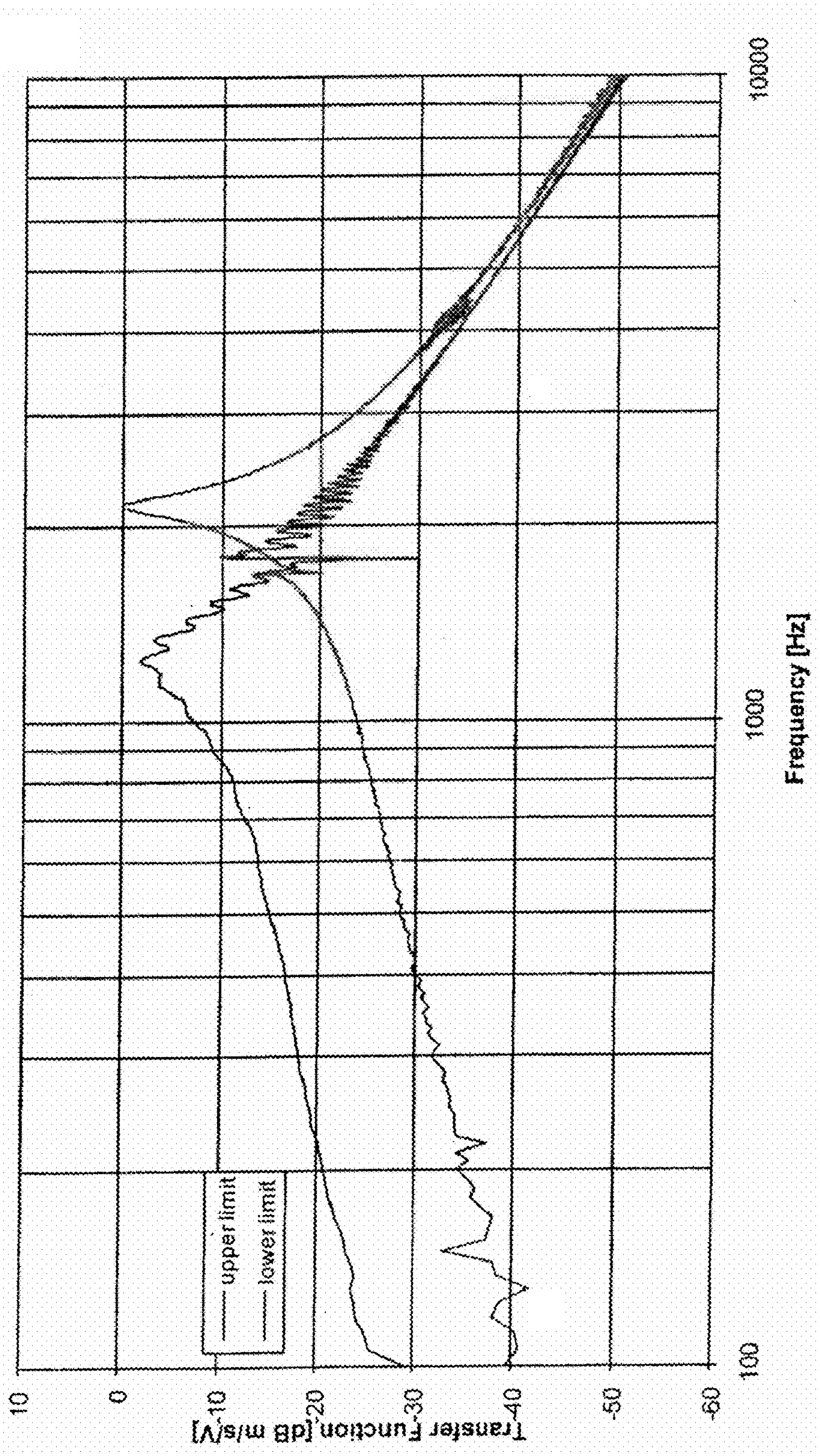
FIG. 2 is an example of the spread of the electromechanical output transducer transfer function.

Fitting of such hearing instrument to the individual user, i.e. determination of the most appropriate gain function, is critical for several reasons. First, the transducer resonance may spread significantly from device to device (this is shown by two examples in FIG. 2). Second, the coupling of the output transducer to the cochlea is not known and may spread significantly from case to case. Third, the output of the output transducer is not available in acoustic form.

Therefore it is necessary to perform a fitting procedure in which the gain function which the hearing instrument applies to the sound signal is adapted to the individual circumstances and requirements of the user of the hearing instrument.

In such fitting procedure audiogram measurements are made wherein loudness perception of a stimulus by the user is tested when using the hearing instrument. In particular, upon having pre-defined a desired target loudness function, measurements are taken of the transducer input audio signal level which has to be applied to the transducer input in order to achieve a certain intermediate perceived loudness level, which preferably is the most comfortable level (MCL). These measurements are repeated for a number of frequencies or frequency bands. Most preferably the measurements for the intermediate loudness level are conducted with a frequency resolution which corresponds to the frequency resolution of the hearing instrument.

Figure 10:
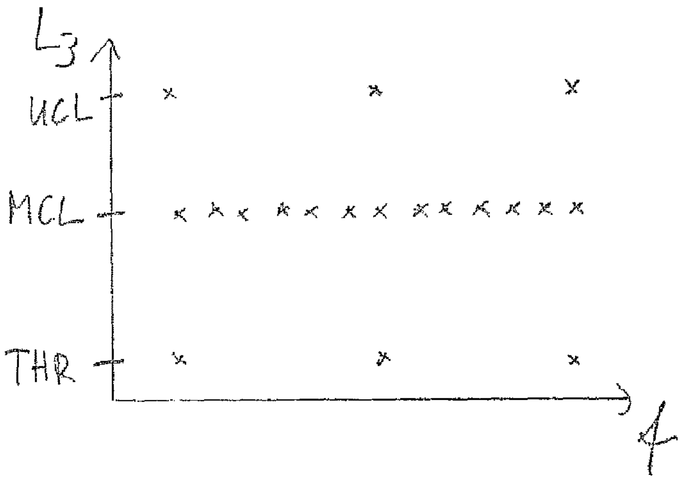
FIG. 10 is a graphical representation of the points of measurement.

As it is indicated in FIG. 10, which illustrates the points where measurements are taken in terms of stimulus frequency f and perceived loudness $L_3$, the measurements of the perceived loudness level preferably are conducted as an equal loudness contour measurement, wherein a transducer input audio signal level $L_2$ is selected such that the same loudness level $L_3$ is perceived by the user.

Figure 11A:
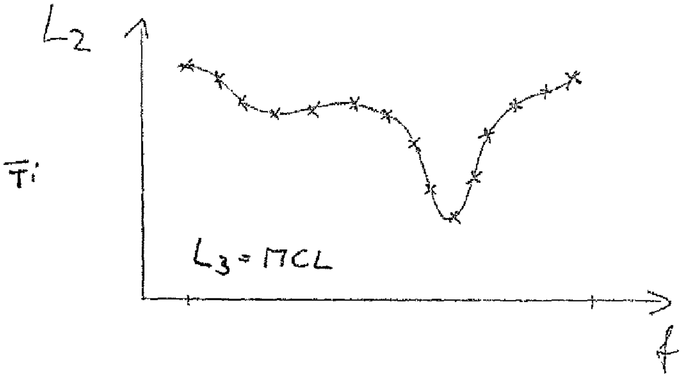
FIG. 11A shows a measuring curve obtained at the most comfortable level (MCL)

FIG. 11A illustrates an exemplary chart of results obtained by the measurements taken at the most comfortable level (MCL) and indicates for each frequency tested the respective transducer input audio signal level $L_2$ that is required to obtain that the constant loudness level $L_3$. As can be seen from FIG. 11A, the transfer function $T_{23}$ which describes the relationship between the transducer input audio signal level $L_2$ and the perceived loudness level $L_3$ is not a linear function but usually shows large variations over the tested frequency range.

Since, however, such variation of the perceived loudness level $L_3$ in the course of the frequency range was found to be largely independent from the loudness level being tested, in the method suggested herein the measurements for low and high loudness levels such as the hearing threshold (THR) and the uncomfortable level (UCL), respectively are restricted to only a few measurement points, for example to only three frequencies, as it is indicated in FIG. 10.

Figure 11B:
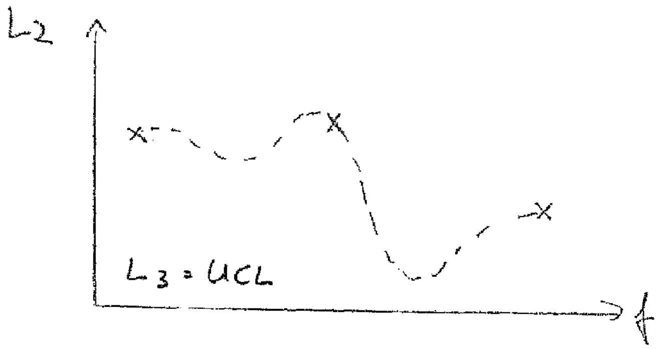
FIG. 11B shows the results obtained by the measurements taken at the most uncomfortable level (UCL), wherein the data curve is obtained by interpolation between the measuring data using the curve shown in FIG. 11A.
Figure 11C:
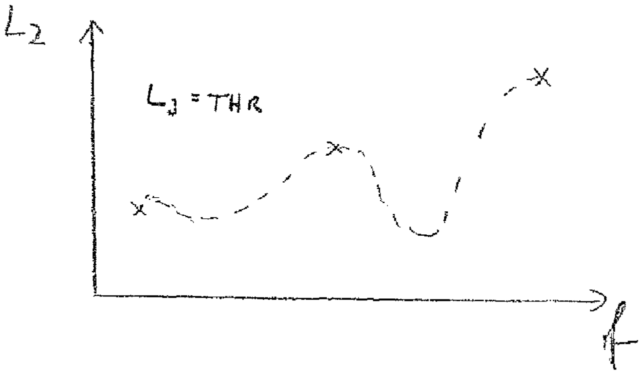

As it is shown in FIGS. 11B and FIG. 11C, using the frequency dependency obtained at high frequency resolution for the intermediate perceived loudness level shown in FIG. 11, curves for the low and high loudness levels are obtained by interpolation between the measurement values taken for the low and high loudness levels at the lower frequency resolution.

In a practical example, the present fitting procedure further may be designed as a two-stage fitting procedure, wherein at the first stage the hearing instrument is used in order to perform audiogram measurements at a few frequencies, whereby some points of the individual loudness curve versus sound input level are obtained between which the individual loudness curve is interpolated. From the individual loudness curve a preliminary individual gain function is calculated which may be used for operating the hearing instrument at the second stage (in particular if the stimulus is provided by an earphone to the microphone 20) wherein at least one contour of equal loudness is measured with a finer frequency resolution than that of the loudness curve of the first stage. The measured contour of equal loudness then is used for correcting the individual preliminary gain function, in particular in between the frequencies already measured in the first stage, in order to consider, for example, the relatively sharp resonance of the output transducer. Thereby from the individual preliminary gain function obtained in the first stage a corrected individual gain function is determined in the second stage, which then is finally used for operating the hearing instrument.

Figure 3:
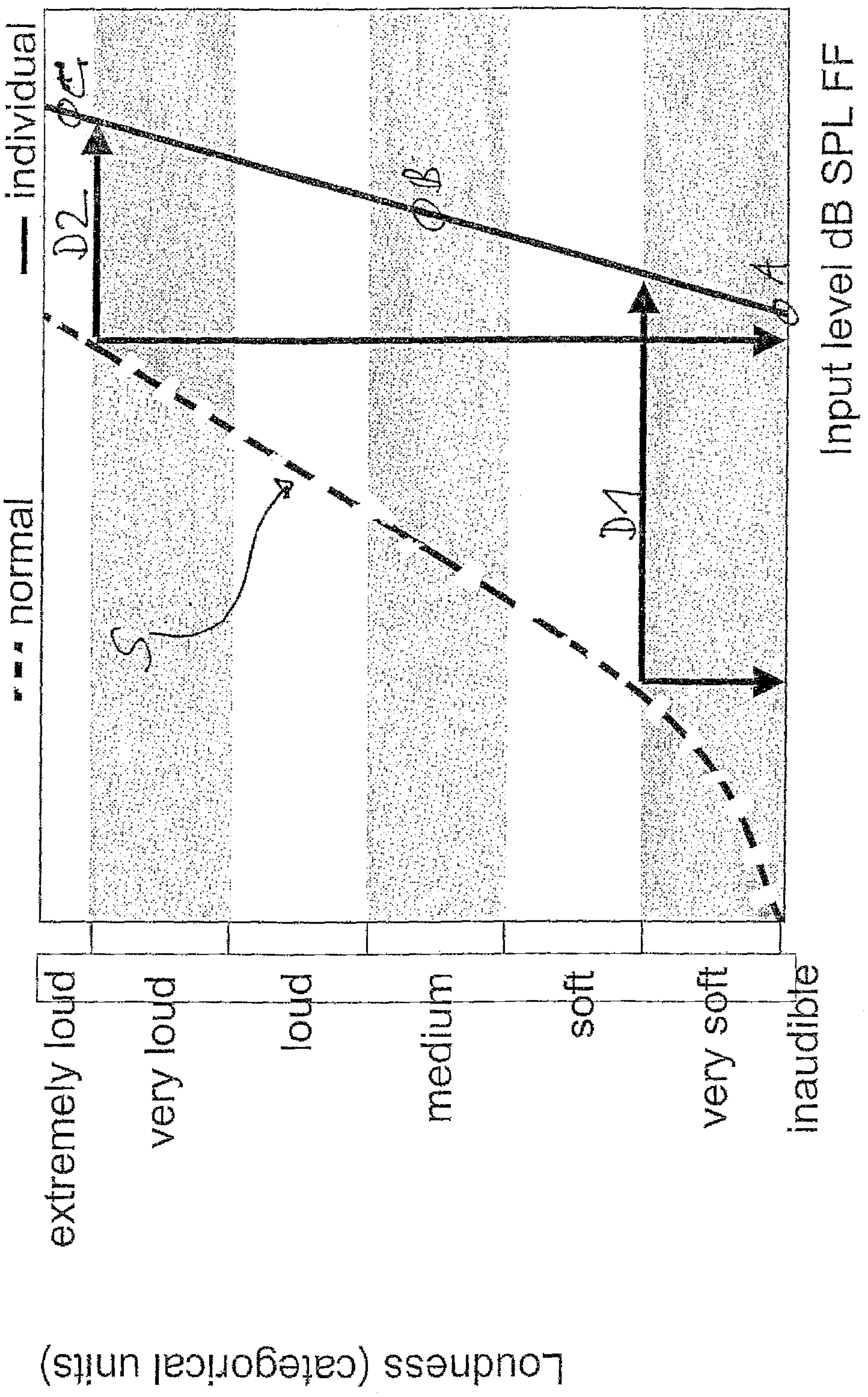
FIG. 3 shows an example of the loudness curve of a normal-hearing person and an measured individual loudness curve of a hearing impaired person using a hearing instrument operated at a preset standard gain function.

The audiogram measurements may be performed such that for each frequency at least two points of the loudness curve are determined, usually the hearing threshold (denoted by A in FIG. 3) and at least one of MCL (denoted by B) and UCL (denoted by C). Such loudness curve as shown in FIG. 3 should be determined at least for four different frequencies spread over the most relevant part of the audible frequencies. The loudness measurements of the first stage are performed with pure sinus tones. While in principle it would be possible to provide the stimulus by an earphone to the microphone 20 (in that case a standard gain function would be used for operating the hearing instrument in the first stage, which preferably is linear with respect to sound input level), it is preferred to generate the stimulus by the sound generator 28 within the control unit 18.

For determining the preliminary individual gain function, at each test frequency the difference between the measured individual loudness curve and the standard loudness curve of the normal hearing person, i.e. the difference in input level necessary for obtaining the same loudness perception, is considered. This is indicated by arrows D1 and D2 in FIG. 3. To this end, the individual loudness curve is interpolated linearly between the measured test input levels. Each input level difference D1 and D2 corresponds to the necessary additional gain at the respective input level of the standard loudness curve (which is labeled S in FIG. 3). The result is shown in FIG. 4 wherein the additional gain relative to the standard gain function necessary for approaching the loudness curve of a normal-hearing person is shown for a given frequency as a function of the input level.

For low input levels the gain may be progressively reduced towards low input levels regarding the values obtained from FIG. 3 in order to implement a function which is known as "soft squelch" and which serves to reduce or eliminate microphone noise otherwise occurring at very low input levels. At high input levels the gain may be progressively reduced towards high input levels relative to the gain determined from FIG. 3 in order to implement a "maximum power output" (MPO) function which serves to avoid uncomfortably high loudness values so that the UCL should not be exceeded.

Figure 4:
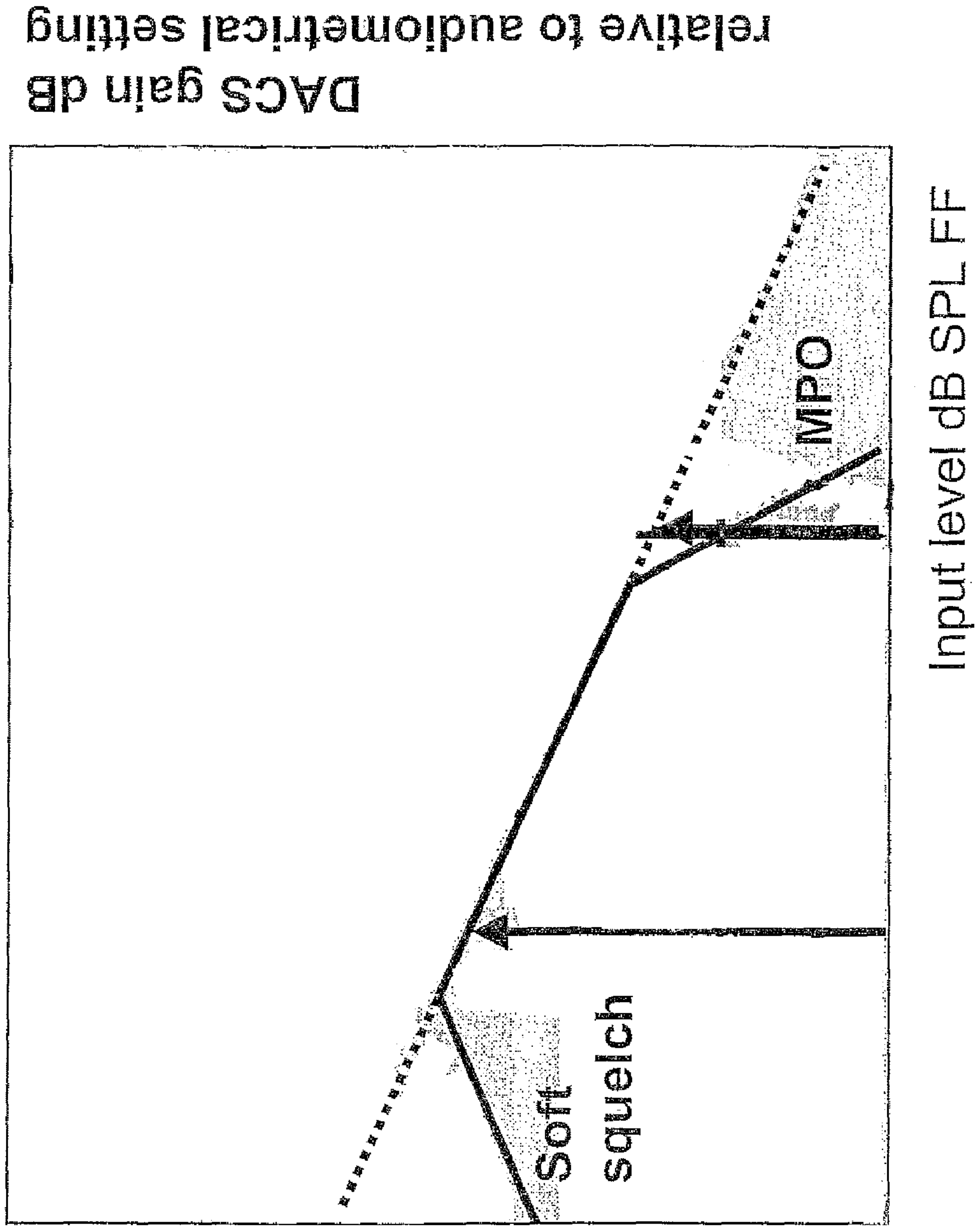
FIG. 4 shows an example of a preliminary individual gain function of the hearing instrument derived from the measured individual loudness curves.

From this first stage measurements for each test frequency an individual preliminary gain function is obtained by adding the standard gain function used during the audiogram measurements to the gain curve shown in FIG. 4.

Figure 5:
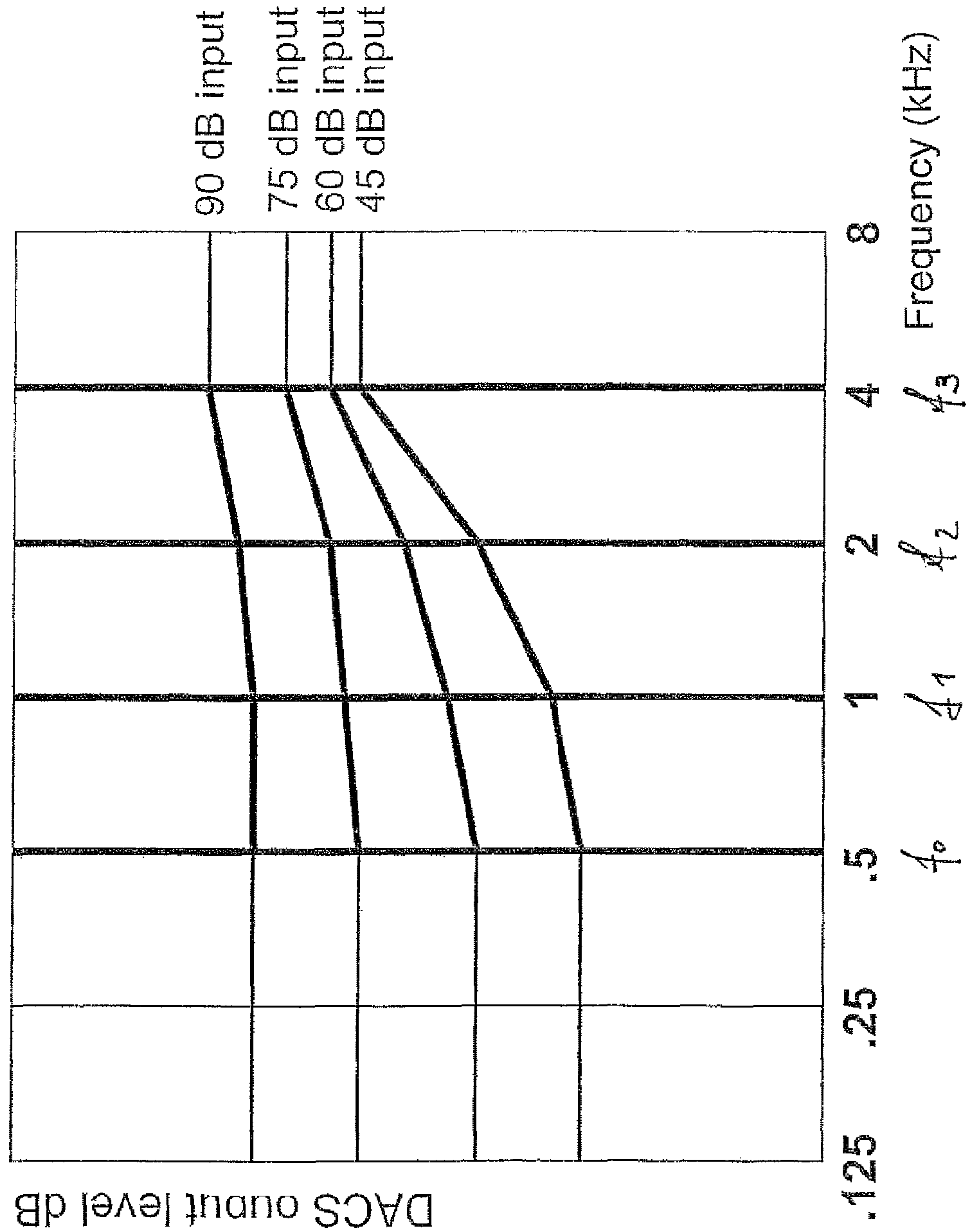
FIG. 5 shows an example of hearing instrument output curves estimated from the measurements of the individual loudness curves as a function of frequency for several input levels.

The obtained data could be represented in an alternative manner as shown in FIG. 5, wherein the transducer output level is plotted as function of frequency for various input levels. Between the test frequencies $f_0$ to $f_3$ the values have been interpolated linearly. The transducer output level shown in FIG. 5 corresponds to the preliminary individual gain of the hearing instrument plus the input level.

At the second stage of the fitting procedure, the hearing instrument is operated with the preliminary individual gain function determined at the first stage in order to measure at least one contour of equal loudness (however, use of preliminary individual gain function for operating the hearing instrument is not necessary if the stimulus is generated by the sound generator 28). Preferably, the contour of equal loudness is measured at the MCL, for example, at 65 phon. In contrast to the audiogram measurements of the first stage, narrow-band noise other than pure sinus tones is used as the stimulus. Analogously to the first stage measurements, the stimulus preferably is provided by the internal sound generator 28 of the control unit 18. In order to determine the contour of equal loudness, for a number of test frequencies the input level of the stimulus is varied until the desired loudness is perceived by the user.

Figure 6:
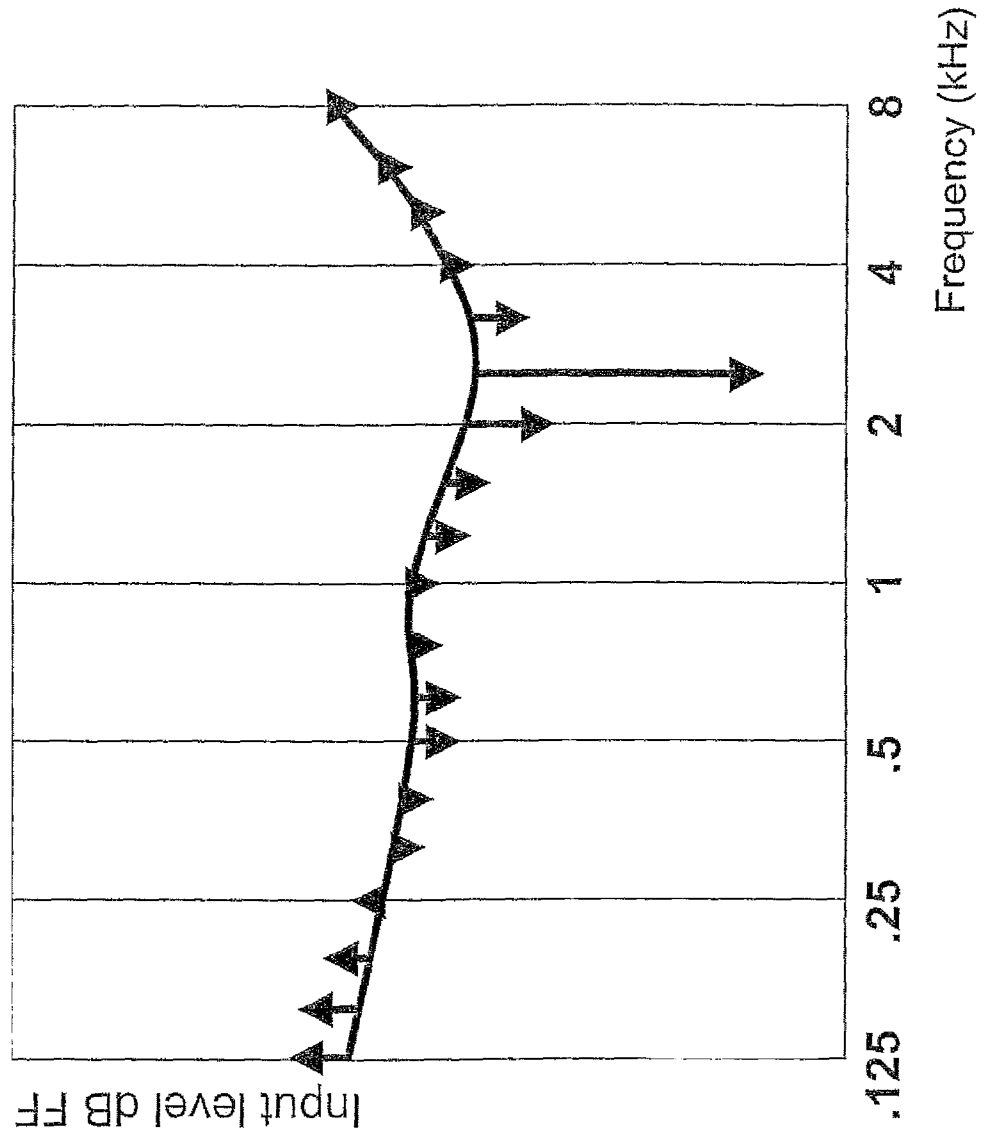
FIG. 6 shows an example of an equal loudness contour of a normal hearing person at 65 phon wherein the input level necessary to achieve this loudness is given as a function of frequency, together with arrows indicating the difference between a measured equal loudness contour of the person using the hearing instrument operated at the preliminary individual gain function to an equal loudness contour estimated by frequency interpolation from the initial loudness measurements.

The test frequencies for the ELC measurements are selected such that the frequency resolution is improved regarding the audiogram measurements of the first stage. In particular, between two of the test frequencies of the first stage at least one test frequency of ELC measurement should be located. In the example shown in FIG. 6, two additional test frequencies of the second stage are located between each pair of adjacent test frequencies of the first stage. Generally, the number of test frequencies of the ELC measurements is higher than the number of test frequencies of the first stage loudness measurements. In the example shown in FIG. 6, twenty test frequencies are used between 0.125 and 8 kHz. The solid line in FIG. 6 shows an example of an ELC of a normal hearing person. The arrows in FIG. 6 represent the difference between the measured ELC and the ELC for the same loudness as estimated from the loudness measurements of the first stage by linear interpolation between the test frequencies of the first stage loudness measurements. In other words, the arrows of FIG. 6 essentially show the deviation of the actually measured ELC from the linear interpolation.

However, even if the test frequencies of the first and second stage measurements coincide, there may be some deviation, since the first stage loudness measurements were performed with pure sinus tones, while the second stage ELC measurements were performed with narrow-band noise, which different stimuli may cause different loudness perception even for the same input level.

It is obvious from FIG. 6 that in the region around 2 kHz the most pronounced deviation from the linear interpolation is observed, which is due to the relatively sharp resonance of the output transducer 32 in that frequency range. Preferably, the ELC measurements include at least five test frequencies between 0.75 and 3 kHz in order to be able to compensate the resonance of the output transducer 32 accurately.

Figure 7:
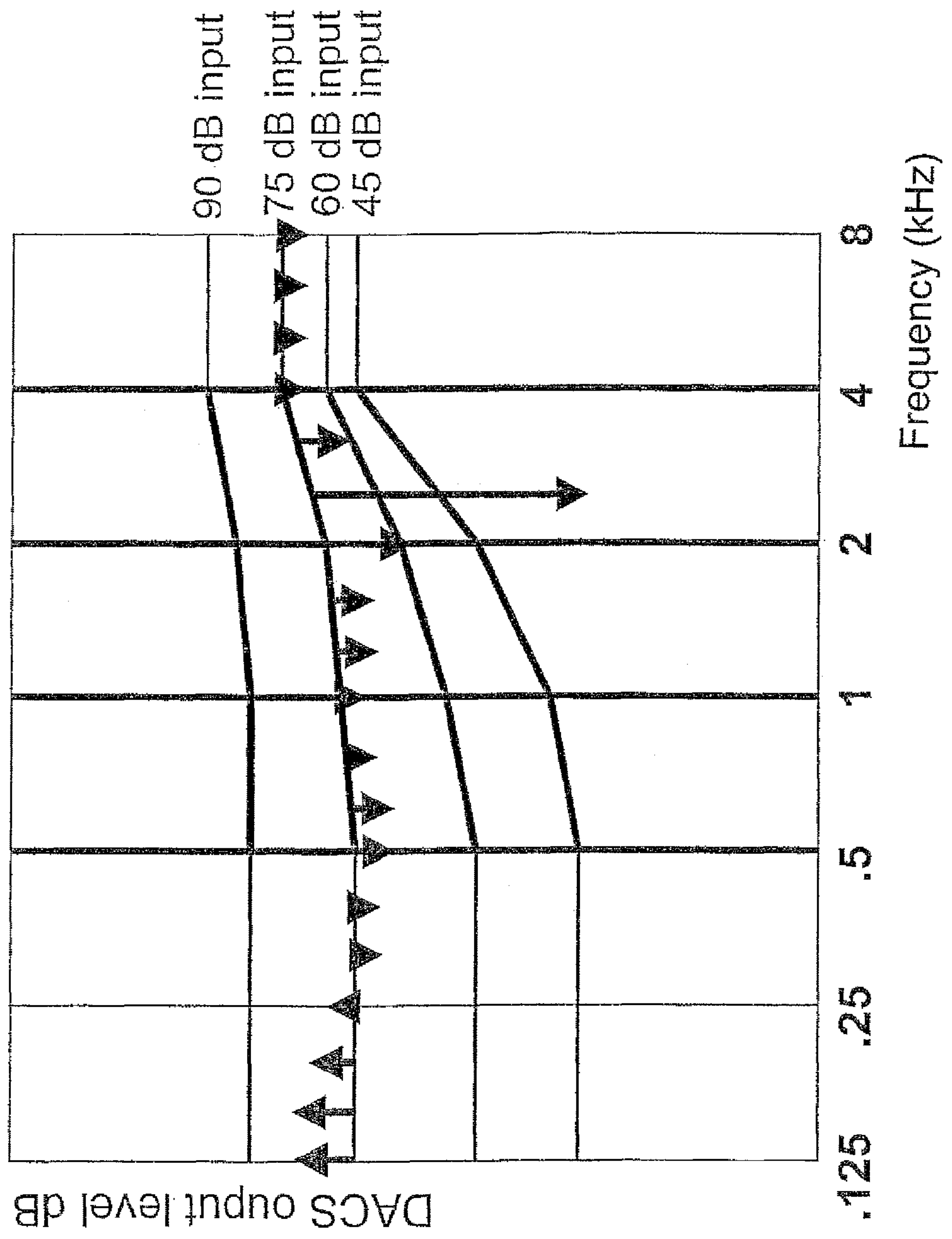
FIG. 7 shows how the obtained differences of the individually measured equal loudness contour curve and the estimated equal loudness contour curve, i.e. the arrows of FIG. 6, are used to correct the 75 dB input level curve.

FIG. 7 is similar to FIG. 5, with the arrows of FIG. 6 having been added to the 75 dB input level curve (the transducer output level is input level times gain provided by the hearing instrument).

Figure 8:
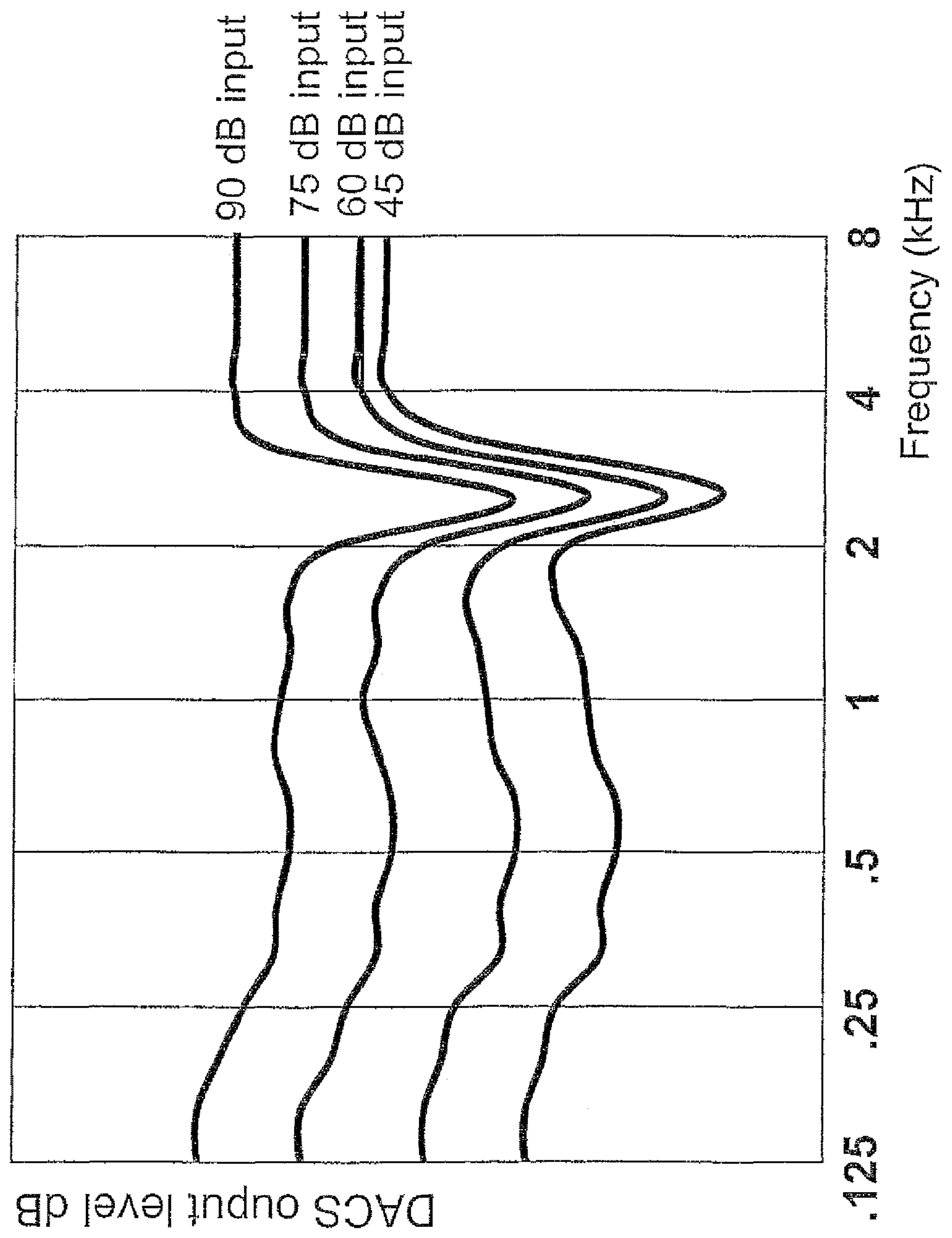
FIG. 8 shows the hearing instrument output curves of FIG. 5 after having been corrected according to the equal loudness contour measurements.

FIG. 8 is a representation similar to FIG. 7, wherein the transducer output level curves have been corrected according to the ELC measurement arrows, with the regions between the test frequencies having been interpolated. Since the output transducer resonance is expected to be linear regarding input level, the corrections obtained from this single ELC measurement can be extrapolated linearly to ELC at other loudness values, so that measurement of ELC for one single loudness is sufficient. This is how the corrected curves at input levels other than 75 dB of FIG. 8 are obtained.

From the transducer output level curves of FIG. 8 the corrected individual gain function can be determined, since the gain function is the ratio of the transducer output level to the input level.

Finally, the hearing instrument is operated with the corrected individual gain function obtained by the above-described fitting procedure.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A method for individually fitting a hearing instrument to a user, comprising at least one microphone for generating an input audio signal from ambient sound, an audio signal processing unit for processing said input audio signal into a processed output audio signal, and a transducer for stimulation of a human auditory system of said user according to said processed output audio signal as input to said transducer, the method comprising:

(a) providing said user with said hearing instrument and starting operation of said hearing instrument;

(b) pre-defining a desired target loudness function, wherein loudness perception of a stimulus by said user when using said hearing instrument is defined as function of frequency and input sound pressure level at said microphone;

(c) measuring for a given measurement parameter set of perceived loudness levels and frequencies or frequency bands, a respective transducer input audio signal level to be applied to an input of said transducer in order to achieve said respective perceived loudness level at said respective frequency or frequency band, said measurement parameter set comprising at least a low loudness level, an intermediate loudness level and a high loudness level, and said intermediate loudness level being measured for a larger number of frequencies or frequency bands and with a finer frequency resolution than said low and high loudness levels;

(d) calculating an individual gain function to be implemented in said audio signal processing unit in order to achieve said pre-defined target loudness function of step (b) by taking into account said transducer input audio signal levels measured in step (c); and (e) operating the hearing instrument with said individual gain function of step (d).

2. The method of claim 1, wherein in step (c) said intermediate loudness level is a most comfortable level, which is an input sound pressure level at which intelligibility of said stimulus by said user is best and to which said user could comfortably listen over an extended period of time.

3. The method of claim 1, wherein in step (c) said low loudness level is a hearing threshold, which is an input sound pressure level at which said stimulus becomes detectable by said user.

4. The method of claim 1, wherein in step (c) said high loudness level is an uncomfortable level, which is an input sound pressure level at which loudness becomes uncomfortable to said user and a sensation of said loudness could not be tolerated for an extended period of time.

5. The method of claim 1, wherein said transducer input audio signal level is measured in step (c) for said intermediate loudness level for at least 8 frequencies or frequency bands.

6. The method of claim 5, wherein said transducer input audio signal level is measured in step (c) for said intermediate loudness level for at least 15 frequencies or frequency bands.

7. The method of claim 1, wherein said transducer input audio signal level is measured in step (c) for said intermediate loudness level at least 5 different frequencies or frequency bands, respectively, in a range from 0.75 to 3 kHz.

8. The method of claim 1, wherein said transducer input audio signal level is measured in step (c) for at least one of said low loudness level and said high loudness level for 3 to 5 frequencies or frequency bands.

9. The method of claim 8, wherein said transducer input audio signal level is measured in step (c) for each loudness level except for said intermediate loudness level for 3 to 5 frequencies or frequency bands.

10. The method of claim 1, wherein said transducer input audio signal level is measured in step (c) for each loudness level for frequencies or frequency bands in a range from 100 to 10,000 Hz.

11. The method of claim 10, wherein said transducer input audio signal level is measured in step (c) for each loudness level for frequencies or frequency bands which are spaced in equal distances in a range from 100 to 10,000 Hz.

12. The method of claim 1, wherein a frequency dependence of values of said transducer input audio signal level as measured in step (c) for said intermediate loudness level is used to interpolate between values of said transducer input audio signal level to be applied to said transducer input as measured in step (c) for said low loudness level and said high loudness level.

13. The method of claim 1, wherein the measurements of step (c) for said intermediate loudness level are conducted as an equal loudness contour measurement, wherein subsequently for each frequency or frequency band a transducer input audio signal level is selected such that a same loudness level is perceived by said user.

14. The method of claim 1, wherein the measurements of step (c) for said low loudness level and said high loudness level are conducted as a series of constant frequency measurements wherein for each frequency or frequency band a transducer input audio signal level is selected such that first said low loudness level and then said high loudness level or first said high loudness level and then said low loudness level is perceived by said user.

15. The method of claim 1, wherein the measurements of step (c) for said intermediate loudness level are conducted with narrow band noise.

16. The method of claim 1, wherein the measurements of step (c) for said low loudness level and said high loudness level are conducted with pure sinus tones.

17. The method of claim 1, wherein values of said transducer input audio signal measured in step (c) for each frequency or frequency band for said intermediate loudness level are interpolated linearly.

18. The method of claim 1, wherein in step (c) said measurement parameter set comprises only said low, intermediate and high loudness levels.

19. The method claim 1, wherein a frequency resolution of the measurements in step (c) for said intermediate loudness level corresponds to a frequency resolution of said hearing instrument.

20. The method of claim 1, wherein in step (c) transducer input audio signal levels are measured for said low loudness level and said high loudness level as an equal loudness contour measurement, wherein subsequently for each frequency or frequency band a transducer input audio signal level is selected such that a same loudness level is perceived by said user a preliminary individual gain function is calculated by taking into account said measured transducer input audio signal levels for said low loudness level and said high loudness level, so as to achieve a pre-defined target loudness function which at least in a range of medium input sound pressure levels corresponds to a standard loudness function of a normal hearing person;

a contour of equal loudness is estimated for said intermediate loudness level from said preliminary individual gain function; and said individual gain function is calculated by correcting said preliminary individual gain function by taking into account a difference between said contour of equal loudness measured in step (c) for said intermediate loudness and said estimated contour of equal loudness.

21. A method for individually fitting a hearing instrument to a user, comprising at least one microphone for generating an input audio signal from ambient sound, an audio signal processing unit for processing said input audio signal into a processed output audio signal, and a transducer for stimulation of a human auditory system of said user according to said processed output audio signal as input to said transducer, the method comprising:

(a) providing said user with said hearing instrument and starting operation of said hearing instrument;

(b) pre-defining a desired target loudness function, wherein loudness perception of a stimulus by said user when using said hearing instrument is defined as function of frequency and input sound pressure level at said microphone;

(c) measuring for a given measurement parameter set of levels of said processed output audio signal and frequencies or frequency bands, a loudness level perceived by said user at said respective frequency or frequency band, said measurement parameter set comprising at least a low audio signal level, an intermediate audio signal level and a high audio signal level, and said intermediate audio signal level being measured for a larger number of frequencies or frequency bands and with a finer frequency resolution than said low and high audio signal levels;

(d) calculating an individual gain function to be implemented in said audio signal processing unit in order to achieve said pre-defined target loudness function of step (b) by taking into said the perceived loudness levels measured in step (c); and (e) operating said hearing instrument with said individual gain function of step (d).

22. The method of claim 21, wherein said perceived loudness level is measured in step (c) for said intermediate audio signal level for at least 8 frequencies or frequency bands.

23. The method of claim 22, wherein said perceived loudness level is measured in step (c) for said intermediate audio signal level for at least 15 frequencies or frequency bands.

24. The method of claim 21, wherein said perceived loudness level is measured in step (c) for said intermediate audio signal level at least 5 different frequencies or frequency bands, respectively, in a range from 0.75 to 3 kHz.

25. The method of claim 21, wherein said perceived loudness level is measured in step (c) for at least one of said low audio signal level and said high audio signal level for 3 to 5 frequencies or frequency bands.

26. The method of claim 24, wherein said perceived loudness level is measured in step (c) for each loudness level except for said intermediate audio signal level for 3 to 5 frequencies or frequency bands.

27. The method of claim 21, wherein said perceived loudness level is measured in step (c) for each audio signal level for frequencies or frequency bands in a range from 100 to 10,000 Hz.

28. The method of claim 27, wherein said perceived loudness level is measured in step (c) for each audio signal level for frequencies or frequency bands which are spaced in equal distances in a range from 100 to 10,000 Hz.

29. The method of claim 21, wherein a frequency dependence of values of said perceived audio signal level as measured in step (c) for said intermediate audio signal level is used to interpolate between values of said perceived loudness level measured in step (c) for said low audio signal level and said high audio signal level.

30. The method of claim 21, wherein the measurements of step (c) for said intermediate audio signal level are conducted with pure sinus tones.

31. The method of one of claims 21 to 30, wherein the measurements of step (c) for said low audio signal level and said high audio signal levels are conducted with narrow band noise.

32. The method of claim 21, wherein values of said perceived loudness level measured in step (c) for each frequency or frequency band for said intermediate audio signal level are interpolated linearly.

33. The method of claim 1, wherein said target loudness function at least in a range of medium input sound pressure levels corresponds to a standard loudness function of a normal hearing person.

34. The method of claim 33, wherein for low input sound pressure levels said target loudness function is progressively reduced towards low input sound pressure levels with respect to said standard loudness function of a normal hearing person.

35. The method of claim 33, wherein for high input sound pressure levels said target loudness function is progressively reduced towards high input sound pressure levels with respect to said standard loudness function of a normal hearing person.

36. The method of claim 1, wherein said transducer input audio signal used in the measurements of step (c) is generated by said audio signal processing unit.

37. The method of claim 1, wherein said transducer input audio signal used in the measurements of step (c) is generated by providing corresponding sound to said microphone.

38. The method of claim 1, wherein said output transducer is an electromechanical output transducer for direct mechanical stimulation of a middle ear or an inner ear.

39. The method of claim 38, wherein said electromechanical output transducer is directly connected in step (a) with a stapes, a footplate of stapes or a cochlea wall.

40. The method of claim 1, wherein said output transducer is an electroacoustic output transducer.

* * * * *